(12) United States Patent
Engh et al.

(10) Patent No.: US 7,494,993 B2
(45) Date of Patent: Feb. 24, 2009

(54) AMIDE DERIVATIVES OF 7-AMINO-3-PHENYL-DIHYDROPYRIMIDO [4,5-D]PYRIMIDINONES, THEIR MANUFACTURE AND USE AS PHARMACEUTICAL AGENTS

(75) Inventors: Richard Engh, Tromsoe (NO); Hubert Hertenberger, Weilheim (DE); Konrad Honold, Penzberg (DE); Birgit Masjost, Basel (CH); Petra Rueger, Penzberg (DE); Wolfgang Schaefer, Mannheim (DE); Stefan Scheiblich, Penzberg (DE); Manfred Schwaiger, Wang-Bergen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 46 days.

(21) Appl. No.: 11/660,197

(22) PCT Filed: Aug. 30, 2005

(86) PCT No.: PCT/EP2005/009322

§ 371 (c)(1),
(2), (4) Date: Feb. 13, 2007

(87) PCT Pub. No.: WO2006/024487

PCT Pub. Date: Mar. 9, 2006

(65) Prior Publication Data

US 2008/0032970 A1 Feb. 7, 2008

(30) Foreign Application Priority Data

Aug. 31, 2004 (EP) .................................. 04020597

(51) Int. Cl.
*C07D 413/14* (2006.01)
*C07D 487/04* (2006.01)
*A61K 31/497* (2006.01)
*A61K 31/519* (2006.01)
*A61K 31/5355* (2006.01)

(52) U.S. Cl. .................... 514/234.2; 544/256; 544/118; 514/252.16; 514/262.1

(58) Field of Classification Search .............. 514/234.2, 514/252.16, 262.1; 544/118, 256
See application file for complete search history.

(56) References Cited

FOREIGN PATENT DOCUMENTS

| WO | WO 99/61444 | 12/1999 |
|----|----|----|
| WO | WO 00/24744 | 5/2000 |
| WO | WO 01/29041 | 4/2001 |
| WO | WO 01/29042 | 4/2001 |
| WO | WO 2004/011465 | 2/2004 |
| WO | WO 2004/018472 | 3/2004 |
| WO | WO 2004/041821 | 5/2004 |
| WO | WO 2004/041822 | 5/2004 |
| WO | WO 2004/041823 | 5/2004 |
| WO | WO 2005/011597 | 2/2005 |

OTHER PUBLICATIONS

Bastin et al., Organic Proc. Res. Dev., 4, pp. 427-435 (2000).
Biscardi et al., Adv. Cancer Res., 76, pp. 61-119 (2000).
Merrifield, R.B., Fed. Proc. Fed. Amer. Soc. Exp. Biol., 21, pp. 412 (1962).
Šuša et al., Trends Pharmaceutical Sci., 21, pp. 489-495 (2000).

*Primary Examiner*—Mark L Berch
*Assistant Examiner*—Cecilia M Jaisle
(74) *Attorney, Agent, or Firm*—George W. Johnston; Patricia S. Rocha-Tramaloni; Gene J. Yao

(57) ABSTRACT

The present invention relates to novel amide derivatives of 7-amino-3-phenyl dihydropyrimido[4,5-d]pyrimidinones, to a process for their manufacture, medicaments containing them and their manufacture as well as the use of these compounds as pharmaceutically active agents. The present derivatives are new compounds of the general formula (I).

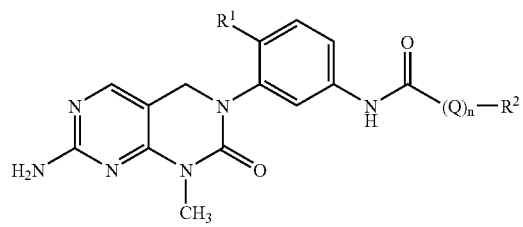

(I)

15 Claims, No Drawings

AMIDE DERIVATIVES OF 7-AMINO-3-PHENYL-DIHYDROPYRIMIDO [4,5-D]PYRIMIDINONES, THEIR MANUFACTURE AND USE AS PHARMACEUTICAL AGENTS

This application is the National Stage of International Application No. PCT/EP2005/009322, filed Aug. 30, 2005, which claims the benefit of European Application NO. 04020597.3, filed Aug. 31, 2004, which is hereby incorporated by reference in its entirety.

The present invention relates to novel amide derivatives of 7-amino-3-phenyl dihydropyrimido[4,5-d]pyrimidinones, to a process for their manufacture, medicaments containing them and their manufacture as well as the use of these compounds as pharmaceutically active agents.

Some substituted bicyclic nitrogen heterocycles are known in the art for their protein kinase, as well as their tyrosine kinase inhibitory activity. WO 01/29042 and WO 01/29041 disclose alkylamino-substituted dihydropyrimido[4,5-d]pyrimidinone derivatives with p38 inhibitory activity. WO 99/61444 describes dihydropyrimido[4,5-d]pyrimidinones, substituted with aryl and heteroarylamines, sulfides, sulfoxides and sulfones as inhibitors for cyclin-dependent kinases (cdks) and tyrosine kinases. Aryl and heteroarylamine substituted dihydropyrimido[4,5-d]pyrimidinones are also described in WO 00/24744 as inhibitors of T-cell tyrosine kinase p56$^{lck}$. Further dihydropyrimido[4,5-d]pyrimidinones with tyrosine kinase inhibitory activity are described in WO 04/18472, WO 04/41821, WO 04/41822, WO 04/41823, and WO 04/11465.

However there remains a need for new compounds with improved therapeutic properties, such as enhanced activity, decreased toxicity, better solubility and improved pharmacokinetic profile, to name only a few.

The present derivatives are new compounds of the general formula I

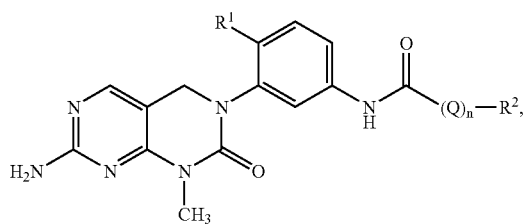

formula I wherein

R$^1$ is hydrogen; fluorine; chlorine; or (C$_1$-C$_3$)alkyl, said acyl being optionally substituted one or several times with halogen;

Q is alkylene or alkenylene;

n is 0 or 1;

R$^2$ is cycloalkyl, aryl or heteroaryl said aryl or heteroaryl being optionally substituted one or two times by phenyl, pyridyl, pyrrolyl or indolyl; and all aromatic groups being optionally substituted one to three times by —CN; —CHO; —OH; —O-alkyl; —NH$_2$; —NH-alkyl; -alkyl-NH$_2$; alkyl; halogen; piperidinyl; piperazinyl; N-methyl-piperazinyl; morpholinyl; 2-dimethylamino-ethoxy; 1-carbamoyl-ethylsulfanyl; N-methyl-piperazinylmethyl; N-acetyl-piperazinylmethyl or morpholinylmethyl; and all pharmaceutically acceptable salts thereof.

The compounds according to this invention show activity as protein kinase inhibitors, in particular src family tyrosine kinase inhibitors, and may therefore be useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, benign hyperplasias and cancer such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

Objects of the present invention are the compounds of formula I and pharmaceutically acceptable salts and their enantiomeric forms, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

The term "alkyl" as used herein means a saturated, straight-chain or branched-chain hydrocarbon containing from 1 to 6, preferably from 1 to 3, carbon atoms, such as methyl, ethyl, n-propyl, isopropyl, n-butyl, 2-butyl, t-butyl.

If said alkyl group is optionally substituted with one or several halogen atoms, it is substituted preferably with fluorine or chlorine, especially fluorine. Examples are difluoromethyl, trifluoromethyl, 2,2,2-triflouro-ethyl, perfluoro-ethyl and the like. The term "halogen" as used herein means fluorine, chlorine and bromine, preferably fluorine or chlorine, especially chlorine.

The term "cycloalkyl" as used herein means a monocyclic saturated hydrocarbon ring with 3 to 7, preferably 5 to 7, ring atoms. Examples of such cycloalkyl groups include cyclopropyl, cyclobutyl, cyclopentyl, cyclohexyl and cycloheptyl, preferably cyclohexyl or cycloheptyl.

The term "aryl" as used herein means a monocyclic or bicyclic aromatic hydrocarbon ring with 6 to 10 ring atoms. such as phenyl, 1-naphthyl or 2-napthtyl.

The term "heteroaryl" as used herein means a mono- or bicyclic aromatic ring with 5 to 10 ring atoms, which contains up to 3, preferably 1 or 2 heteroatoms selected independently from N, O or S and the remaining ring atoms being carbon atoms. Examples of such heteroaryl groups include pyrrolyl, thiophenyl, furyl, thiazolyl, oxazolyl, isoxazolyl, pyrazolyl, imidazolyl; pyridyl, pyrimidinyl, pyrazinyl, pyridazinyl, indolyl, benzothiophenyl, benzothiazolyl, benzoxazolyl, benzimidazolyl, quinolyl, isoquinolyl and the like, especially isoxazolyl, pyrazolyl, pyridyl, indolyl or benzothiophenyl.

The term "alkylene" as used herein means a saturated, straight-chain or branched-chain, preferably straight-chain hydrocarbon containing from 1 to 5, preferably from 1 to 3, carbon atoms, such as methylene, ethylene, trimethylene; tetramethylene)pentamethylene, methylmethylene, 1-methyl-ethylene, 2-methyl-ethylene, 1-ethyl-ethylene, 2-ethyl-ethylene, 1-propyl-ethylene, 2-propyl-ethylene, 1-methyl-trimethylene, 2-methyl-trimethylene, 1-ethyl-trimethylene, 2-ethyl-trimethylene, especially methylene, ethylene or trimethylene.

The term "alkenylene" as used herein means an unsaturated, straight-chain or branched-chain, preferably straight-chain hydrocarbon containing from 2 to 6, preferably from 2 to 3, carbon atoms. Examples of such "alkenylenes" are vinylene(ethenylene), allylene, isopropenylene, 1-propenylene, 2-methyl-1-propenylene, 1-butenylene, 2-butenylene, 3-butenylene, 2-ethyl-1-butenylene, 3-methyl-2-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene and 5-hexenylene especially vinylene(ethenylene), allylene, isopropenylene, 1-propenylene, 2-methyl-1-propenylene.

Preferably in all embodiments of the invention $R^1$ is chlorine.

A preferred embodiment of the invention are the compounds according to formula I, wherein $R^2$ is cycloalkyl, aryl or heteroaryl said aryl or heteroaryl being optionally substituted one or two times by phenyl, pyridyl; pyrrolyl or indolyl; and all aromatic groups being optionally substituted one to three times by —CN; —CHO; —OH; —O-alkyl; —NH$_2$; —NH-alkyl; -alkyl-NH$_2$; alkyl; halogen; piperidinyl; piperazinyl; N-methyl-piperazinyl or morpholinyl;

A preferred embodiment of the invention are the compounds according to formula I, wherein n is 0.

A preferred embodiment of the invention are the compounds according to formula I, wherein n is 0; and $R^2$ is cycloalkyl, aryl or heteroaryl said aryl or heteroaryl being optionally substituted one or two times by phenyl, pyridyl; pyrrolyl or indolyl; and all aromatic groups being optionally substituted one to three times by —CN; —CHO; —OH; —O-alkyl; —NH$_2$; —NH-alkyl; -alkyl-NH$_2$; alkyl; halogen; piperidinyl; piperazinyl; N-methyl-piperazinyl or morpholinyl;

Another preferred embodiment of the invention are the compounds according to formula I, wherein n is 1.

A preferred embodiment of the invention are the compounds according to formula 1, wherein n is 1; and $R^2$ is cycloalkyl, aryl or heteroaryl said aryl or heteroaryl being optionally substituted one or two times by phenyl, pyridyl; pyrrolyl or indolyl; and all aromatic groups being optionally substituted one to three times by —CN; —CHO; —OH; —O-alkyl; —NH$_2$; —NH-alkyl; -alkyl-NH$_2$; alkyl; halogen; piperidinyl; piperazinyl; N-methyl-piperazinyl or morpholinyl;

A preferred embodiment of the invention are the compounds according to formula I, wherein $R^2$ is cycloalkyl.

Another preferred embodiment of the invention are the compounds according to formula I, wherein n is 0; and $R^2$ is cycloalkyl.

Such compounds are for example:

Cyclohexanecarboxylic acid (4-chloro-3-{7-amino-1-methyl-2-oxo-1,4-dihydro-2H-pyrimido[4,5-d]pyrimidin-3-yl}-phenyl)-amide; compound with acetic acid; and Cycloheptanecarboxylic acid (4-chloro-3-{7-amino-1-methyl-2-oxo-1,4-dihydro-2H-pyrimido[4,5-d]pyrimidin-3-yl}-phenyl)-amide; compound with acetic acid.

Another preferred embodiment of the invention are the compounds according to formula I, wherein $R^2$ is aryl, said aryl being optionally substituted one or two times by phenyl, pyridyl; pyrrolyl or indolyl;

and all aromatic groups being optionally substituted one to three times by —CN; —CHO; —OH; —O-alkyl; —NH$_2$; —NH-alkyl; -alkyl-NH$_2$; alkyl; halogen; piperidinyl; piperazinyl; N-methyl-piperazinyl or morpholinyl.

Still another preferred embodiment of the invention are the compounds according to formula I, wherein n is 0; and $R^2$ is phenyl, said phenyl being substituted one or two times by phenyl or pyridyl; and all aromatic groups being optionally substituted one to three times by —CN; —CHO; —OH; —O-alkyl; —NH$_2$; —NH-alkyl; -alkyl-NH$_2$; alkyl or halogen.

Such compounds are for example:

Biphenyl-4-carboxylic acid(4-chloro-3-{7-amino-1-methyl-2-oxo-1,4-dihydro-2H-pyrimido[4,5-d]pyrimidin-3-yl}-phenyl)-amide; and Biphenyl-2-carboxylic acid(4-chloro-3-{7-amino-1-methyl-2-oxo-1,4-dihydro-2H-pyrimido[4,5-d]pyrimidin-3-yl}-phenyl)-amide; compound with acetic acid; and Biphenyl-3-carboxylic acid(4-chloro-3-{7-amino-1-methyl-2-oxo-1,4-dihydro-2H-pyrimido[4,5-d]pyrimidin-3-yl}-phenyl)-amide; compound with acetic acid; and 4'-Cyano-biphenyl-3-carboxylic acid(4-chloro-3-{7-amino-1-methyl-2-oxo-1,4-dihydro-2H-pyrimido[4,5-d]pyrimidin-3-yl}-phenyl)-amide.

Such compounds are for example:

N-[3-(7-Amino-1-methyl-2-oxo-1,4-dihydro-2H-pyrimido[4,5-d]pyrimidin-3-yl)-4-chloro-phenyl]-4-pyridin-2-yl-benzamide; and N-[3-(7-Amino-1-methyl-2-oxo-1,4-dihydro-2H-pyrimido[4,5-d]pyrimidin-3-yl)-4-chloro-phenyl]-4-pyridin-4-yl-benzamide.

Still another preferred embodiment of the invention are the compounds according to formula I, wherein n is 0; and $R^2$ is phenyl said phenyl being substituted one time by phenyl; and all phenyl groups being substituted one time by 2-dimethylamino-ethoxy; 1-carbamoyl-ethylsulfanyl; N-methyl-piperazinylmethyl; N-acetyl-piperazinylmethyl or morpholinylmethyl.

Such compounds are for example:

4'-Morpholin-4-ylmethyl-biphenyl-4-carboxylic acid[3-(7-amino-1-methyl-2-oxo-1,4-dihydro-2H-pyrimido[4,5-d]pyrimidin-3-yl)-4-chloro-phenyl]-amide;

3'-(4-Methyl-piperazin-1-ylmethyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide;

3'-(4-Acetyl-piperazin-1-ylmethyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide;

3'-Morpholin-4-ylmethyl-biphenyl-4-carboxylic acid[3-(7-amino-1-methyl-2-oxo-1,4-dihydro-2H-pyrimido[4,5-d]pyrimidin-3-yl)-4-chloro-phenyl]-amide;

3'-(1-Carbamoyl-ethylsulfanyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide; and 3'-(2-Dimethylamino-ethoxy)-biphenyl-4-carboxylic acid [3-(7-amino-1-methyl-2-oxo-1,4-dihydro-2H-pyrimido[4,5-d]pyrimidin-3-yl)-4-chloro-phenyl]-amide; compound with acetic acid.

Another preferred embodiment of the invention are the compounds according to formula I, wherein n is 0; and $R^2$ is phenyl, said phenyl being optionally substituted one or two times by pyrrolyl or indolyl; and all aromatic groups being optionally substituted one to three times by —CN; —CHO; —OH; —O-alkyl; —NH2; —NH-alkyl; -alkyl-NH2; alkyl or halogen.

Such a compound is for example:

N-[3-(7-Amino-1-methyl-2-oxo-1,4-dihydro-2H-pyrimido[4,5-d]pyrimidin-3-yl)-4-chloro-phenyl]-4-(1H-pyrrol-2-yl)-benzamide.

Another preferred embodiment of the invention are the compounds according to formula I, wherein n is 0; and $R^2$ is phenyl, said phenyl being optionally substituted one to three times by —CN; —CHO; —OH; —O-alkyl; $NH_2$; —NH-alkyl; halogen; piperidinyl; piperazinyl; N-methyl-piperazinyl or morpholinyl.

Such compounds are for example:

N-[3-(7-Amino-1-methyl-2-oxo-1,4-dihydro-2H-pyrimido[4,5-d]pyrimidin-3-yl)-4-chloro-phenyl]-4-(4-methyl-piperazin-1-yl)-benzamide; an N-[3-(7-Amino-1-methyl-2-oxo-1,4-dihydro-2H-pyrimido[4,5-d]pyrimidin-3-yl)-4-chloro-phenyl]-4-morpholin-4-yl-benzamide; and N-[3-(7-Amino-1-methyl-2-oxo-1,4-dihydro-2H-pyrimido[4,5-d]pyrimidin-3-yl)-4-chloro-phenyl]-4-cyano-benzamide.

Another preferred embodiment of the invention are the compounds according to formula I, wherein n is 1; and $R^2$ is phenyl, said phenyl being optionally substituted one to three times by —CN; —CHO; —OH; —O-alkyl; $NH_2$; —NH-alkyl; halogen.

Still another preferred embodiment of the invention are the compounds according to formula I, wherein Q is alkylene;

n is 1; and $R^2$ is phenyl, said phenyl being optionally substituted one to three times by —CN; —CHO; —OH; —O-alkyl; $NH_2$; —NH-alkyl or halogen.

Such compounds are for example:

N-[3-(7-Amino-1-methyl-2-oxo-1,4-dihydro-2H-pyrimido[4,5-d]pyrimidin-3-yl)-4-chloro-phenyl]-4-phenyl-butyramide; and N-[3-(7-Amino-1-methyl-2-oxo-1,4-dihydro-2H-pyrimido[4,5-d]pyrimidin-3-yl)-4-chloro-phenyl]-3-phenyl-propionamide; and N-[3-(7-Amino-1-methyl-2-oxo-1,4-dihydro-2H-pyrimido[4,5-d]pyrimidin-3-yl)-4-chloro-phenyl]-3-(2-hydroxy-phenyl)-propionamide; and N-[3-(7-Amino-1-methyl-2-oxo-1,4-dihydro-2H-pyrimido[4,5-d]pyrimidin-3-yl)-4-chloro-phenyl]-3-(3-aminophenyl)-propionamide; and N-[3-(7-Amino-1-methyl-2-oxo-1,4-dihydro-2H-pyrimido[4,5-d]pyrimidin-3-yl)-4-chloro-phenyl]-3-(4-aminophenyl)-propionamide.

Still another preferred embodiment of the invention are the compounds according to formula I, wherein Q is alkenylene;

n is 1; and $R^2$ is phenyl, said phenyl being optionally substituted one to three times by —CN; —CHO; —OH; —O-alkyl; $NH_2$; —NH-alkyl or halogen.

Such a compound is for example:

N-[3-(7-Amino-1-methyl-2-oxo-1,4-dihydro-2H-pyrimido[4,5-d]pyrimidin-3-yl)-4-chloro-phenyl]-3-phenyl-acrylamide.

Still another preferred embodiment of the invention are the compounds according to formula I, wherein n is 0; and $R^2$ is naphtyl, said naphtyl being optionally substituted one or two times by phenyl; and all aromatic groups being optionally substituted one to three times by —CN; —CHO; —OH; —O-alkyl; $NH_2$; —NH-alkyl or halogen.

Such a compound is for example:

Naphthalene-1-carboxylic acid[3-(7-amino-1-methyl-2-oxo-1,4-dihydro-2H-pyrimido[4,5-d]pyrimidin-3-yl)-4-chloro-phenyl]-amide.

Another preferred embodiment of the invention are the compounds according to formula I, wherein n is 0; and $R^2$ is pyridyl; isoxazolyl or pyrazolyl; and said is pyridyl; isoxazolyl or pyrazolyl one or two times by phenyl or pyridyl; and all aromatic groups being optionally substituted one to three times by —CN; —CHO; —OH; —O-alkyl; —$NH_2$; —NH-alkyl; -alkyl-$NH_2$; alkyl or halogen.

Still another preferred embodiment of the invention are the compounds according to formula I, wherein n is 0; and $R^2$ is indolyl or benzothiophenyl; and said indolyl or benzothiophenyl being optionally substituted one to three times by —CN; —CHO; —OH; —O-alkyl; —$NH_2$; —NH-alkyl; -alkyl-$NH_2$; alkyl or halogen.

Such a compound is for example:

1H-Indole-2-carboxylic acid[3-(7-amino-1-methyl-2-oxo-1,4-dihydro-2H-pyrimido[4,5-d]pyrimidin-3-yl)-4-chloro-phenyl]-amide.

Such a compound is for example:

Benzo[b]thiophene-2-carboxylic acid (4-chloro-3-{7-amino-1-methyl-2-oxo-1,4-dihydro-2H-pyrimido[4,5-d]pyrimidin-3-yl}-phenyl)-amide.

Still another preferred embodiment of the invention are the compounds according to formula I, wherein Q is alkylene;

n is 1; and $R^2$ is pyridyl; said pyridyl being optionally substituted one or two times by —CN; —CHO; —OH; —O-alkyl; —$NH_2$; —NH-alkyl; -alkyl-$NH_2$; alkyl or halogen.

Such compounds are for example:

N-[3-(7-Amino-1-methyl-2-oxo-1,4-dihydro-2H-pyrimido[4,5-d]pyrimidin-3-yl)-4-chloro-phenyl]-2-pyridin-3-yl-acetamide; and N-[3-(7-Amino-1-methyl-2-oxo-1,4-dihydro-2H-pyrimido[4,5-d]pyrimidin-3-yl)-4-chloro-phenyl]-2-pyridin-2-yl-acetamide; and N-[3-(7-Amino-1-methyl-2-oxo-1,4-dihydro-2H-pyrimido[4,5-d]pyrimidin-3-yl)-4-chloro-phenyl]-3-pyridin-3-yl-propionamide.

Still another preferred embodiment of the invention are the compounds according to formula I, wherein Q is alkenylene;
n is 1; and
$R^2$ is pyridyl; said pyridyl being optionally substituted one or two times by —CN; —CHO; —OH; —O-alkyl; —$NH_2$; —NH-alkyl; -alkyl-$NH_2$; alkyl or halogen.

Such a compound is for example:

N-[3-(7-Amino-1-methyl-2-oxo-1,4-dihydro-2H-pyrimido[4,5-d]pyrimidin-3-yl)-4-chloro-phenyl]-3-pyridin-2-yl-acrylamide.

Still another embodiment of the invention is a process for the manufacture of the compounds according to this invention. Said compounds can be prepared (a) by reacting the amino group in the compounds of the general formula II

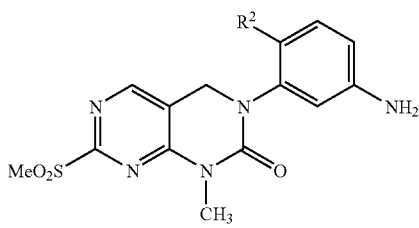

II wherein $R^2$ has the meaning given herein before with a carboxylic acid of the general formula III

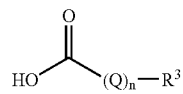

III wherein $R^3$ has the meaning given herein before to give the amide derivative of formula IV

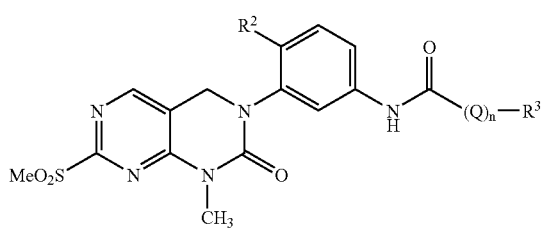

IV (b) the methylsulfonyl group is converted to the corresponding amine to give the compounds of the general formula I

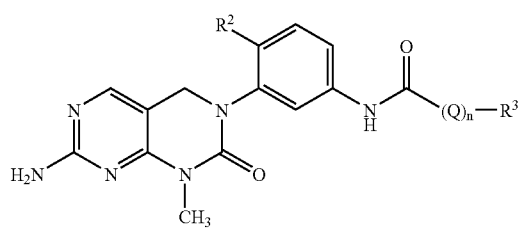

I (c) if desired converting said compound of the general formula I into a pharmaceutically acceptable salt.

The compounds of formula I, or a pharmaceutically acceptable salt thereof, which are subject of the present invention may be prepared by any process known to be applicable to the preparation of chemically-related compounds. Such processes, when used to prepare a 7-amino-3-phenyl dihydropyrimido[4,5-d]pyrimidinone derivative of the formula I, or a pharmaceutically-acceptable salt thereof, are illustrated by the following representative schemes and examples in which, unless otherwise stated, $R^1$, $R^2$, and $R^3$ have the significance defined hereinbefore. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

The compounds of formula I can be prepared from 4-chloro-2-methylsulfanyl-pyrimidine-5-carboxylic acid ethyl ester, which is known from WO 04/41823, according to schemes 1, 2, and 3, wherein $R^1$, $R^2$, and $R^3$ have the significance given above.

Scheme 1

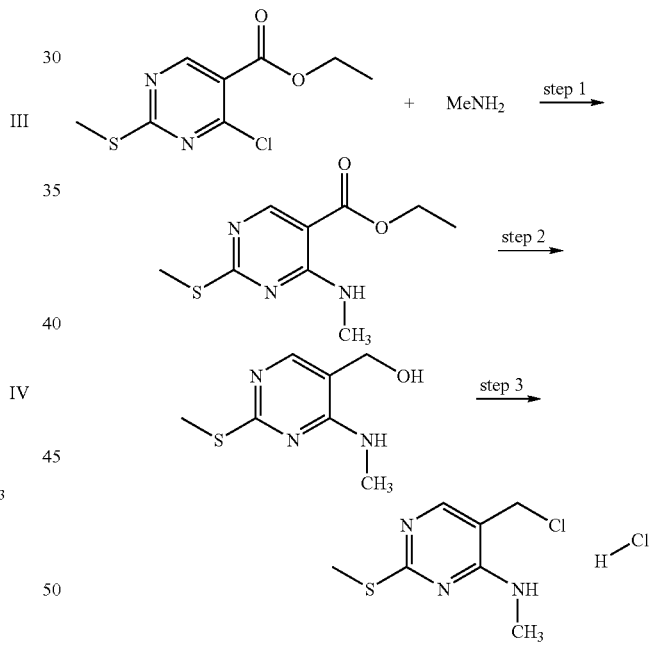

Step 1:

4-Methylamino-2-methylsulfanylpyrimidine-5-carboxylic acid ethyl ester was prepared from 4-chloro-2-methylsulfanyl-pyrimidine-5-carboxylic acid ethyl ester and methylamine in tetrahydrofuran (THF) under basic conditions with triethylamine at temperatures between 5° C. and room temperature (RT).

Step 2:

(4-Methylamino-2-methylsulfanyl-pyrimidin-5-yl)-methanol was prepared by reduction of 4-methylamino-2-methylsulfanylpyrimidine-5-carboxylic acid ethyl ester with lithium aluminiumhydride in tetrahydrofuran (THF) at temperatures ranging from 5° C. to room temperature (RT).

Step 3:

(4-Methylamino-2-methylsulfanyl-pyrimidin-5-yl)-methanol was converted to (5-chloromethyl-2-methylsulfanyl-pyrimidin-4-yl)-methyl-amine with thionyl chloride in 1,1,1-trichloroethane at room temperature.

Step 4:

(5-Chloromethyl-2-methylsulfanyl-pyrimidin-4-yl)-methyl-amine was reacted with compounds of the formula VI by the addition of sodium iodide and N-ethyldiisopropylamine in acetonitrile or in solvents of similar polarity at a temperature range between −20° C. and 180° C. to give compounds of the formula VII.

Step 5:

Compounds of formula VIII can be prepared from compounds of formula VII by treatment with 1,1'-carbonyldiimidazole and potassium carbonate ($K_2CO_3$) at a temperature range from 0° C. to 180° C. in acetonitrile or in solvents of similar polarity such as dimethyl formamide (DMF) or tetrahydrofuran (THF). Alternatively, e.g. sodium hydride in dimethyl formamide/tetrahydrofuran can be used.

Step 6:

A methylthio group can be converted into the suitable leaving group by oxidation to the sulfoxide. Compounds of formula VIII are converted to compounds of formula IX with 3-chloroperoxybenzoic acid (mCPBA) as oxidizing reagent in an inert solvent such as dichloromethane ($CH_2Cl_2$), THF or NMP at a temperature range from 0° C. to 150° C. to give compounds of formula (IX).

Step 7:

The compounds of formula IX are reduced to compounds of formula II by hydrogenation using deactivated Pd(CaCO3)/C or other Pd catalysts. The reduction takes place at a temperature range between 0° C. and 150° C. in inert solvents such as THF, $CH_2Cl_2$, or NMP.

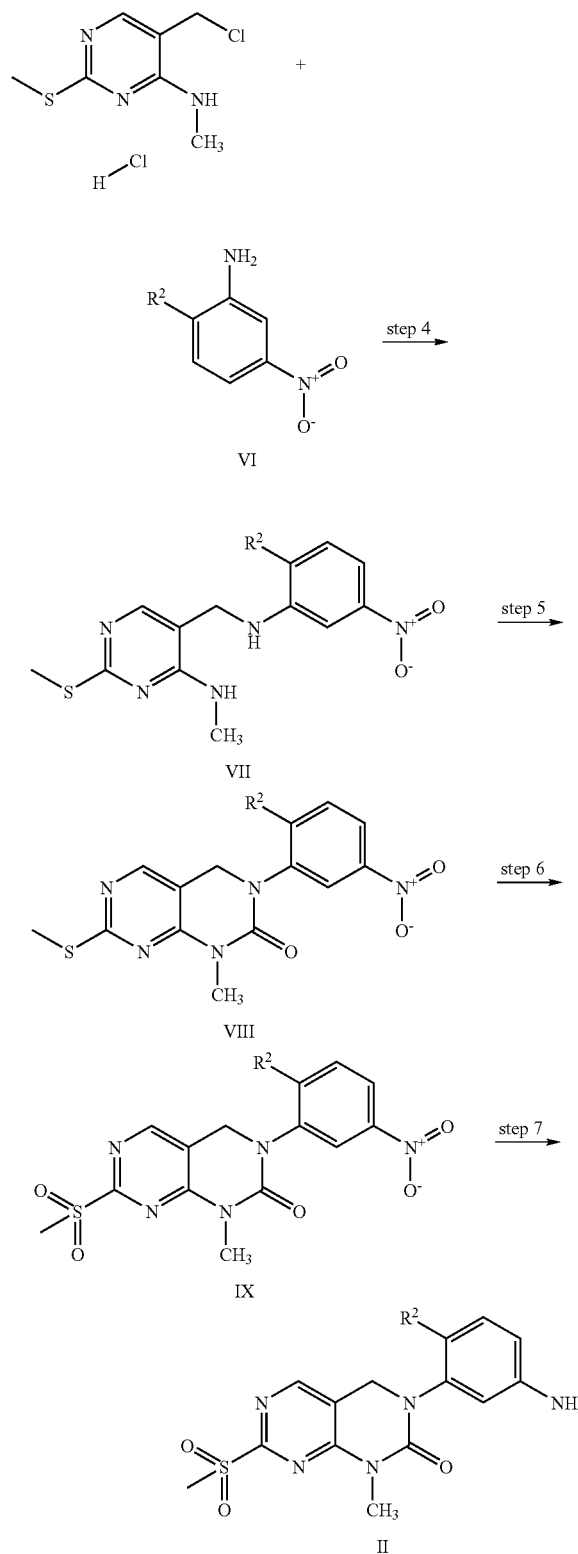

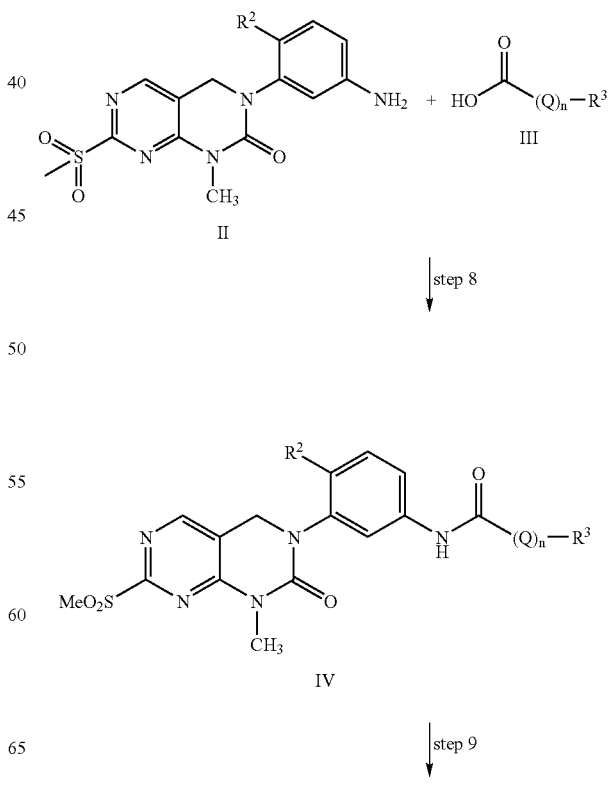

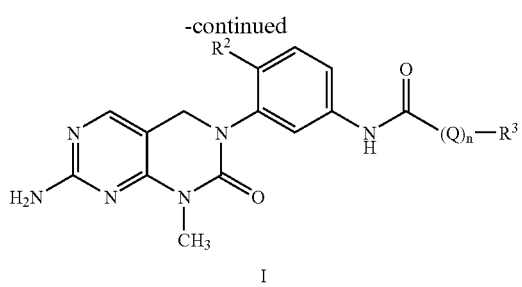

I

Step 8:

Compounds of formula II are coupled to carboxylic acids of formula III to give the amides of formula IV. Common reagents for the activation of carboxylic acid were used such as e.g. 1-(3-dimethylaminopropyl)-3-ethylcarbodiimide hydrochloride (EDCI), N,N'-dicyclohexylcarbodiimide (DCC), 1-hydroxybenzotriazole (HOBT), N,N'-carbonyldiimidazole (CDI), and 4-(4,6-dimethoxy-[1,3,5]triazin-2yl)-4-methyl-morpholin-4-ium chloride (DMTMM) in inert solvents such as THF, $CH_2Cl_2$, or NMP or in polar solvents such methanol (MeOH) or even water. Sometimes dimethylaminopyridine (DMAP) was added as a catalyst. Another method of activation is the preparation of the corresponding acid chlorides. The condensation reaction may be carried out under basic conditions. e.g. in the presence of triethylamine, N,N-diisopropylethylamine (Hünig base). Some acids bearing functional groups which were not stable under the reaction conditions were protected with standard protection groups such as t-butoxycarbonyl (Boc) or benzyloxycarbonyl.

Step 9:

The compounds of formula IV are transformed into compounds of formula I by treatment with ammonia. One method consists of autoclaving a solution of compound IV and liquid ammonia and stirring at a temperature range of −20-100° C. until the transformation is complete. An alternative method comprises of treatment of a solution of compound IV with an aqueous solution of ammonia under a continuous flow of gaseous ammonia.

Certain side chains in $R^3$ may require protection during the reaction sequences. Here standard protection and deprotection procedures being well known in the art may be applied. For instance, primary and secondary amines can be applied in t-butoxycarbonyl (Boc) or benzyloxycarbonyl protected form and the protecting group can be removed as a last reaction step by treatment with an acid like HCl or TFA.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Stahl, P. H., and Wermuth, G., (editors), Handbook of Pharmaceutical Salts, Verlag Helvetica Chimica Acta (VHCA), Zürich, (2002) or Bastin, R. J., et al. Organic Proc. Res. Dev. 4 (2000) 427-435.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical preparation is obtained by using the following procedure:

1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.

9. Repeat washing with small volumes(here 1 ml steps) until final volume is reached or extract is clear.
10. Fill up to final volume with gelatin and homogenise.

The above described preparation procedure yields microsuspensions of the compounds of formula I with particle sizes between 1 and 10 μm. The suspensions are suitable for oral applications and can be used in the in vivo pharmacokinetic testings.

Pharmacological Activity:

The activity of the compounds according to this invention as inhibitors for the src-family tyrosine kinases was shown by using the following assay.

SRC-Inhibitor-Assay Parameters:
Reaction mixture:
ATP 5 μM
Peptide (Ro+Ja133-Ro): 10 μM
   Ja133-Ro 196 nM
   Ro 9.8 μM
PT66 230 ng/ml
Assay buffer: 4 mM MgCl2
   2 mM TCEP
   50 mM HEPES
   0.1% Tween 20
   pH 7.3
Enzyme: 2.5 U/ml
Inhibitor: max. 25 μM
   min. 0.42 nM
Material:
Eu-labelled phosphotyrosine antibody: for Lck Cisbio Mab PT66-K,
   for Src EG&G Wallac PT66 Eu-W1024 (all commercially available).
Peptides: Ro: $NH_2$-A-E-E-E-I-Y-G-E-F-E-A-K-K-K-K-$CONH_2$, and
   Ja133-Ro: Ja133-G-Aminocaprylic acid-A-E-E-E-I-Y-G-E-F-E-A-K-K-K-K-$CONH_2$, wherein Ja133 is LightCycler-Red 640-N-hydroxy succinimide ester;
   whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 μmol scale) of a Rink-Linker modified polystyrene solid phase by repeatedly conjugating an twenty fold excess of amino acids each protected by temporary piperidine labile Fmoc- and permanent acid labile tert-Bu-, BOC- and O-tert-Bu-groups depending on the side chain function. The substrate sequence AEEEIYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification.

The purification yielded 12.2 mg RP-HPLC single peak pure blue material (lyophilisate). The identity was proven by MALDI mass spectroscopy [2720.0].

Enzymes: Upstate Lck (p56[kk], active), Upstate Src (p60[c-src], partially purified) were purchased from UBI, Upstate Biotech, Inc.

Time-resolved Fluorescence Assay: Reader: Perkin Elmer, Wallac Viktor 1420-040 multilabel counter; Liquid handling system: Beckman Coulter, Biomek 2000.

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK))

| Ex.-No. | IC50 src (nM) | IC50 lck (nM) |
| --- | --- | --- |
| 2-7 | 73.5 | 168 |
| 2-14 | 41 | 38.5 |
| 1, 2-3, 2-15, 2-22, 2-24 | 50-150 | 50-150 |

Medicaments containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their tyrosine kinase inhibition and their antiproliferative activity, said compounds are useful for the treatment of diseases such as cancer in humans or animals and for the production of corresponding medicaments. The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

EXAMPLES

A: Starting Materials

Example a

{5-[(2-Chloro-5-nitro-phenylamino)-methyl]-2-methylsulfanyl-pyrimidin-4-yl}-methyl-amine 15.85 g (5-Chloromethyl-2-methylsulfanyl-pyrimidin-4-yl)-methyl-amine hydrochloride, 1.979 g sodium iodide, and 34.49 mL N—N-diisopropylethylamine were solved in 150 ml acetonitrile and cooled to 0° C. 17.085 g 2-Chloro-5-nitrophenylamine dissolved in 150 ml acetonitrile were added slowly under stirring. The reaction mixture was stirred at room temperature for 48 hrs, then the solvent was evaporated. The residue was solved in a mixture of water/acetic acid ethyl ester (1:1), stirred and the crystalline product was isolated by filtration and dried for 48 h under vacuum at 40° C. The two phases of the mother liquor were separated and the aqueous phase was extracted with dichloromethane. The organic phases were combined, dried over sodium sulfate, the solvent was evaporated and the residue was rubbed with diethyl ether. Both residues were combined and gave of the title product in 97% yield.

$^1$H-NMR (400 MHz, CDCl$_3$): δ=7.9540 (1H); 7.6400-7.5991 (2H); 7.4579-7.4359 (1H); 4.4058-4.3940 (1H); 4.1932-4.1806 (2H); 3.0746-3.0416 (3H); 2.5723-2.5279 (3H)

Example b 3-(2-Chloro-5-nitro-phenyl)-1-methyl-7-methylsulfanyl-3,4-dihydro-1H-pyrimido[4,5-d]pyrimidin-2-one 20.796 g {5-[(2-Chloro-5-nitro-phenylamino)-methyl]-2-methylsulfanyl-pyrimidin-4-yl}-methyl-amine were dissolved in 500 ml acetonitrile, 25.375 g potassium carbonate and 19.847 g N,N-carbonyldiimidazole (CDI) were added, and the solution was heated at 50° C. for 24 hrs. The solvent was dried over sodium sulfate, evaporated, and the residue was extracted with diethyl ether to give the title product in 96% yield.

Example c 3-(2-Chloro-5-nitro-phenyl)-7-methanesulfonyl-1-methyl-3,4-dihydro-1H-pyrimido[4,5-d]pyrimidin-2-one 1.4 g 3-(2-Chloro-5-nitro-phenyl)-1-methyl-7-methylsulfanyl-3,4-dihydro-1H-pyrimido[4,5-d]pyrimidin-2-one were dissolved in 75 ml dichloromethane, cooled to 0° C., and 3.305 g meta-chloroperbenzoic acid (mCPBA) were added. The mixture was stirred for 24 h at room temperature. Then the reaction mixture was quenched by extraction with 150 mL of an aqueous solution of potassium carbonate. The organic phase was separated, dried over sodium sulfate and the solvent was evaporated. The residue was extracted with diethyl ether and the title product obtained in 70% yield.

$^1$H-NMR (400 MHz, CDCl$_3$): δ=8.4417-7.7268 (4H); 4.8703-4.8451 (2H); 3.5581 (3H); 3.3765 (3H)

Example d 3-(5-Amino-2-chloro-phenyl)-7-methanesulfonyl-1-methyl-3,4-dihydro-1H-pyrimido[4,5-d]pyrimidin-2-one 5.94 g 3-(2-chloro-5-nitro-phenyl)-7-methanesulfonyl-1-methyl-3,4-dihydro-1H-pyrimido[4,5-d]pyrimidin-2-one were dissolved in 200 mL tetrahydrofuran. Pd(CaCO3)/C was added to the solution which was then treated with hydrogen (1 atm) for 18 h. The solution was then filtrated and the solvent evaporated. The residue was extracted with diethyl ether and the title product obtained in 98% yield.

Example e

Biphenyl-4-carboxylic acid[4-chloro-3-(7-methanesulfonyl-1-methyl-2-oxo-1,4-dihydro-2H-pyrimido[4,5-d]pyrimidin-3-yl)-phenyl]-amide 0.2 g 3-(5-Amino-2-chloro-phenyl)-7-methanesulfonyl-1-methyl-3,4-dihydro-1H-pyrimido[4,5-d]pyrimidin-2-one were dissolved in 50 mL of dichloromethane. 0.137 g Biphenyl-4-carboxylic acid and 0.042 g 4-dimethylaminopyridine (DMAP) were added. The solution was cooled to 0° C. and 0.128 g N-(3-dimethylaminopropyl)-N-ethylcarbodiimide hydrochloride (EDCI), dissolved in 20 mL dichloromethane were slowly added. The reaction mixture was stirred for 24 h under nitrogen. The reaction was quenched by extraction with 100 mL of an aqueous solution of potassium carbonate. The phases were separated, the aqueous phase was extracted with dichloromethane, and the combined organic phases were dried over sodium sulfate and evaporated. The crude product was purified by flash chromatography on silica gel (n-heptane/ethyl acetate (EtOAc)) to give the title product in 28% yield.

$^1$H-NMR (400 MHz, CDCl$_3$): δ=8.3772-7.3794 (14H); 4.9021-4.7663 (2H); 3.5745-3.5592 (3H); 3.3662 (3H)

Example f

4'-Morpholin-4-ylmethyl-biphenyl-4-carboxylic acid [4-chloro-3-(7-methanesulfonyl-1-methyl-2-oxo-1,4-dihydro-2H-pyrimido[4,5-d]pyrimidin-3-yl)-phenyl]-amide 300 mg of 4'-Morpholin-4-ylmethyl-biphenyl-4-carboxylic acid in 15 ml dry tetrahydrofuran (THF) were treated dropwise with 129 mg oxalyl chloride under cooling with ice. The mixture was subsequently stirred for 20 min at room temperature (RT) before a suspension of 200 mg aniline derivative from example d in 5 ml dichloromethane was added slowly. The mixture was stirred over night and then diluted with 50 ml dichloromethane. Precipitate was filtered off and the filtrate was washed several times with conc. aqueous sodium carbonate solution. The organic phase was dried, evaporated and purified by flash chromatography on silica, using a gradient from dichloromethane to dichloromethane/methanol (60/1) to dichloromethane/methanol/concentrated ammonia (60/1/0.2).

Yield 56 mg of the title product

Example g

3'-Morpholin-4-ylmethyl-biphenyl-4-carboxylic acid [4-chloro-3-(7-methanesulfonyl-1-methyl-2-oxo-1,4-dihydro-2H-pyrimido[4,5-d]pyrimidin-3-yl)-phenyl]-amide 0.48 g 3'-Morpholin-4-ylmethyl-biphenyl-4-carboxylic acid were dissolved in 40 ml thionylchloride. 1 drop of dimethylformamide (DMF) was added and the mixture stirred at 50 C for 1 hr. The excess thionyl chloride was removed under vacucum and the residue was taken up in a mixture of 5 ml THF and 5 ml N-methyl-pyrrolidinone (NMP). 0.21 g of the aniline derivative from example d were added at RT and the mixture was stirred for 2 hrs. The solvents were removed under vacuum at 80 C, and the residue was diluted with 120 ml dichloromethane and washed several times with conc. aqueous sodium carbonate solution. Evaporation and chromatography on silica using a gradient from dichloromethane to dichloromethane/methanol/conc. ammonia (70/1/0.5) yielded 120 mg of the title product.

Substituted biphenyl carboxylic acids were prepared as know from the literature or according to the following procedures:

Example h 2-(3-Bromo-phenylsulfanyl)-propionamide

To a mixture of 5.0 g 3-bromobenzenethiol and 5.96 g potassium carbonate in 50 ml DMF were added 3.86 g 2-bromopropionamide at RT. The mixture was warmed up and stirred at 70 C for 3.5 hrs. After cooling, 200 ml water were added and the mixture extracted 3 times with dichloromethane. Drying and evaporation of the organic phases yielded 6.5 g of the title product which was used without further purification.

Example i

3'-(1-Carbamoyl-ethylsulfanyl)-biphenyl-4-carboxylic acid 3.0 g of the substituted bromo-benzene from example f, 1.95 g of 4-carboxybenzeneboronic acid, and 8.05 g potassium carbonate were stirred in a mixture of 25 ml dioxane and 25 ml water. 1.35 g tetrakis-triphenylphosphino-palladium were added under nitrogen atmosphere and the mixture was heated 85 C for 14 hrs. The mixture was diluted with 40 ml water and filtered. The filtrate was adjusted to pH 2 with conc. HCl and the precipitated product isolated by filtration. Yield 2.8 g

Example j 1-(3-Bromo-benzyl)-4-methyl-piperazine 0.30 g 1-Methylpiperazine in 2 ml THF were treated dropwise at RT with a solution of 0.5 g 3-bromobenzyl bromide in 3 ml THF. After stirring for 2 hrs, the mixture was heated to 60 C for 30 min. The solvent was evaporated and the residue chromatographed on silica using a gradient from heptane to heptane/dichloromethane/concentrated ammonia (4/6/0.5).
Yield 0.16 g of the title product

Example k

3'-(4-Methyl-piperazin-1-ylmethyl)-biphenyl-4-carboxylic acid 98 mg 4-Carboxybenzeneboronic acid, 159 mg substituted bromobenzene from example h, 410 mg potassium carbonate, and 69 mg tetrakis-triphenylphosphino-palladium were stirred under an argon atmosphere in a mixture of 1 ml dioxane and 1 ml water at 85 C for 16 hrs. The mixture was cooled to RT, diluted with 100 ml water and filtered. The filtrate was carefully treated with conc. HCl until the product precipitated. Filtration and drying of the residue yielded 190 mg of the title product.

B: Final Products

Example 1

Biphenyl-4-carboxylic acid[3-(7-amino-1-methyl-2-oxo-1,4-dihydro-2H-pyrimido[4,5-d]pyrimidin-3-yl)-4-chloro-phenyl]-amide 0.079 g Biphenyl-4-carboxylic acid[4-chloro-3-(7-methanesulfonyl-1-methyl-2-oxo-1,4-dihydro-2H-pyrimido[4,5-d]pyrimidin-3-yl)-phenyl]-amide were dissolved in 10 mL tetrahydrofuran. 10 mL of liquid ammonia were added in an autoclave and the reaction mixture was stirred for 2 h. The organic solvent was evaporated, and the crude product was purified by reverse phase chromatography (acetonitrile/water with 1% acetic acid) to give the title product in 31% yield.

$^1$H-NMR (400 MHz, [$D_6$]-DMSO): δ=10.52 (s, 1H); 8.06 (m, 3H); 7.96 (s, 1H); 7.86 (d, 2H); 7.82-7.70 (m, 3H); 7.57 (d, 1H); 7.52 (m, 2H); 7.43 (t, 1H); 6.61 (s, 2H); 4.60 (d, 1H); 4.49 (d, 1H); 3.26 (s, 3H).

Example 2

According to the synthesis procedure described in Example 1 and using the corresponding starting materials, the following compounds can be obtained:

| Example-No. | Compound name | $^1$H-NMR |
|---|---|---|
| 2-1 | Cyclohexanecarboxylic acid [3-(7-amino-1-methyl-2-oxo-1,4-dihydro-2H-pyrimido[4,5- | (400 MHz, [$D_6$]-DMSO): δ = 10.0627 (1H); 7.9340-1.4677 (4H); 6.6162 (2H); 4.5678-4.4221 |

-continued

| Example-No. | Compound name | $^1$H-NMR |
|---|---|---|
| | d]pyrimidin-3-yl)-4-chloro-phenyl]-amide | (2H); 3.2373 (3H); 1.6629-1.1942 (11H) |
| 2-2 | Cycloheptanecarboxylic acid [3-(7-amino-1-methyl-2-oxo-1,4-dihydro-2H-pyrimido[4,5-d]pyrimidin-3-yl)-4-chloro-phenyl]-amide | (400 MHz, CDCl$_3$): δ = 7.9412-7.0906 (4H); 5.0537 (2H); 4.5681-4.4137 (2H); 3.3357 (3H); 2.0138-0.7839 (14H) |
| 2-3 | Biphenyl-3-carboxylic acid [3-(7-amino-1-methyl-2-oxo-1,4-dihydro-2H-pyrimido[4,5-d]pyrimidin-3-yl)-4-chloro-phenyl]-amide | (400 MHz, [D$_6$]-DMSO): δ = 10.5596 (1H); 8.2300-7.1858 (13H); 6.6217 (2H); 4.6198-4.4742 (2H); 3.2555 (3 H) |
| 2-4 | Biphenyl-2-carboxylic acid [3-(7-amino-1-methyl-2-oxo-1,4-dihydro-2H-pyrimido[4,5-d]pyrimidin-3-yl)-4-chloro-phenyl]-amide | (400 MHz, [D$_6$]-DMSO): δ = 10.5051 (1H); 7.9291-7.3682 (13H); 6.5899 (2H); 4.5467-4.4078 (2H); 3.2261 (3 H) |
| 2-5 | 4'-Cyano-biphenyl-4-carboxylic acid [3-(7-amino-1-methyl-2-oxo-1,4-dihydro-2H-pyrimido[4,5-d]pyrimidin-3-yl)-4-chloro-phenyl]-amide | (400 MHz, [D$_6$]-DMSO): δ = 10.5932 (1H); 8.1213-7.5844 (12H); 4.6483-4.4997 (2H); 3.2913-3.2799 (3 H); |
| 2-6 | N-[3-(7-Amino-1-methyl-2-oxo-1,4-dihydro-2H-pyrimido[4,5-d]pyrimidin-3-yl)-4-chloro-phenyl]-4-(4-methyl-piperazin-1-yl)-benzamide | (400 MHz, CDCl$_3$): δ = 8.33887 (1H); 7.85875-7.77275 (4H); 7.35813-7.28661 (2H); 6.89079-6.86848 (2H); 5.46509 (2H); 4.61538-4.47385 (2H); 3.40267-3.33837 (7H); 2.65554-2.38177 (7H) |
| 2-7 | N-[3-(7-Amino-1-methyl-2-oxo-1,4-dihydro-2H-pyrimido[4,5-d]pyrimidin-3-yl)-4-chloro-phenyl]-4-morpholin-4-yl-benzamide | (400 MHz, CDCl$_3$): δ = 8.43679 (1H); 7.85855-6.86089 (8H); 5.43902 (2H); 4.60859-4.46688 (2H); 3.87301-3.84903 (4H); 3.44919-3.40874 (3H); 3.36292-3.24756 (4H) |
| 2-8 | N-[3-(7-Amino-1-methyl-2-oxo-1,4-dihydro-2H-pyrimido[4,5-d]pyrimidin-3-yl)-4-chloro-phenyl]-4-cyano-benzamide | (400 MHz, [D$_6$]-DMSO): δ = 10.7113 (1H); 8.1254-7.5822 (8H); 6.6135 (2H); 4.6157-4.4653 (2H); 3.2556 (3 H) |
| 2-9 | N-[3-(7-Amino-1-methyl-2-oxo-1,4-dihydro-2H-pyrimido[4,5-d]pyrimidin-3-yl)-4-chloro-phenyl]-4-phenyl-butyramide | (400 MHz, CDCl$_3$): δ = 8.2997 (1H); 7.8091 (1H); 7.6078 (1H); 7.2795-7.0839 (6 H); 5.4568 (2H); 4.6203-4.4604 (2H); 3.3827 (3H); 2.6814-2.6439 (2H); 2.2645-1.9395 (4H) |
| 2-10 | N-[3-(7-Amino-1-methyl-2-oxo-1,4-dihydro-2H-pyrimido[4,5-d]pyrimidin-3-yl)-4-chloro-phenyl]-3-phenyl-propionamide | (400 MHz, CDCl$_3$): δ = 8.3229 (1H); 7.8428-7.1710 (9H); 5.1254 (2H); 4.6283-4.4604 (2H); 3.3893 (3H); 2.9792-2.8415 (2H); 2.5870-2.5469 (2H) |
| 2-11 | N-[3-(7-Amino-1-methyl-2-oxo-1,4-dihydro-2H-pyrimido[4,5-d]pyrimidin-3-yl)-4-chloro-phenyl]-3-(2-hydroxy-phenyl)-propionamide | (400 MHz, [D$_4$]-Methanol): δ = 7.97291-6.70022 (8H); 4.60250-4.53118 (2H); 3.30625-3.30303 (3H); 2.98709-2.64581 (4H) |
| 2-12 | N-[3-(7-Amino-1-methyl-2-oxo-1,4-dihydro-2H-pyrimido[4,5-d]pyrimidin-3-yl)-4-chloro-phenyl]-3-(3-amino-phenyl)-propionamide | (400 MHz, [D$_4$]-Methanol): δ = 6.67704-5.93583 (8H); 3.557818 (3H); 2.15970 (2H); 3.37838 (2H); 1.80427-1.76730 (2H); 1.47763-1.44051 (2H) |
| 2-13 | N-[3-(7-Amino-1-methyl-2-oxo-1,4-dihydro-2H-pyrimido[4,5-d]pyrimidin-3-yl)-4-chloro-phenyl]-3-(4-amino-phenyl)-propionamide | (400 MHz, [D$_4$]-Methanol): δ = 6.45957-6.39919 (2H); 5.99341-5.80747 (6H); 3.4441 (3H); 3.16662 (2H); 1.94942 (2H); 1.57740-1.54010 (2H); 1.24110-1.20355 (2H) |
| 2-14 | N-[3-(7-Amino-1-methyl-2-oxo-1,4-dihydro-2H-pyrimido[4,5-d]pyrimidin-3-yl)-4-chloro-phenyl]-3-phenyl-acrylamide | (400 MHz, [D$_6$]-DMSO): δ = 10.4693 (1H); 7.9503-7.3142 (9H); 6.8414-6.6129 (3H); 4.6159-4.4526 (2H); 3.2564 (3H); |
| 2-15 | Naphthalene-1-carboxylic acid [3-(7-amino-1-methyl-2-oxo- | (400 MHz, CDCl$_3$): δ = 8.68929-7.18332 (11H); 4.53073-4.37536 |

-continued

| Example-No. | Compound name | ¹H-NMR |
|---|---|---|
| | 1,4-dihydro-2H-pyrimido[4,5-d]pyrimidin-3-yl)-4-chloro-phenyl]-amide | (2H); 3.71563 (2 H); 3.07453 (3H) |
| 2-16 | 1H-Indole-2-carboxylic acid [3-(7-amino-1-methyl-2-oxo-1,4-dihydro-2H-pyrimido[4,5-d]pyrimidin-3-yl)-4-chloro-phenyl]-amide | (400 MHz, CDCl₃): δ = 9.1832 (1H); 8.3118 (1H); 7.8047-7.0049 (9H); 5.0057 (2 H); 4.5665-4.4793 (2H); 3.4220 (3H) |
| 2-17 | N-[3-(7-Amino-1-methyl-2-oxo-1,4-dihydro-2H-pyrimido[4,5-d]pyrimidin-3-yl)-4-chloro-phenyl]-2-pyridin-3-yl-acetamide | (400 MHz, CDCl₃): δ = 8.8753 (1H); 8.4845-8.4319 (2H); 7.7457-7.0875 (6H); 5.3675 (2H); 4.5733-4.3916 (2H); 3.4878 (2H); 3.3779 (3H) |
| 2-18 | N-[3-(7-Amino-1-methyl-2-oxo-1,4-dihydro-2H-pyrimido [4,5-d]pyrimidin-3-yl)-4-chloro-phenyl]-2-pyridin-2-yl-acetamide | (400 MHz, CDCl₃): δ = 10.1276 (1H); 8.5660-8.5548 (1H); 7.7849-7.2637 (6H); 55219 (2H); 4.6124-4.4677 (2H); 3.8654 (2H); 3.3734 (3H) |
| 2-19 | N-[3-(7-Amino-1-methyl-2-oxo-1,4-dihydro-2H-pyrimido[4,5-d]pyrimidin-3-yl)-4-chloro-phenyl]-3-pyridin-3-yl-propionamide | (400 MHz, CDCl₃): δ = 8.62096-8.45120 (4H); 7.80166-7.13461 (4H); 5.54711 (2 H); 4.62781-4.45806 (2H); 3.59510 (3H); 2.99458-2.95718 (2H); 2.56850-2.53039 ( 2H) |
| 2-20 | N-[3-(7-Amino-1-methyl-2-oxo-1,4-dihydro-2H-pyrimido[4,5-d]pyrimidin-3-yl)-4-chloro-phenyl]-3-pyridin-2-yl-acrylamide | (400 MHz, [D₆]-DMSO): δ = 8.6561-8.6460 (1H); 7.9446-7.2951 (8H); 6.6081 (2H); 4.6124-4.4479 (2H); 3.2519-3.2371 (3H) |
| 2-21 | Benzo[b]thiophene-2-carboxylic acid (4-chloro-3-{7-amino-1-methyl-2-oxo-1,4-dihydro-2H-pyrimido[4,5-d]pyrimidin-3-yl}-phenyl)-amide | (400 MHz, [D₆]-DMSO): δ = 10.94 (s, 1H); 8.56 (s, 1H); 8.25-8.15 (m, 3H); 7.94 (dd, 1H); 7.78 (d, 1H); 7.69-7.65 (m, 3H); 7.30 (br s, 2H); 4.81 (d, 1H); 4.69 (d, 1H); 3.45 (s, 3H); |
| 2-22 | N-[3-(7-Amino-1-methyl-2-oxo-1,4-dihydro-2H-pyrimido[4,5-d]pyrimidin-3-yl)-4-chloro-phenyl]-4-pyridin-2-yl-benzamide | (400 MHz, [D₆]-DMSO): δ = 10.57(s, 1H); 8.73 (br s, 1H); 8.25 (d, 2H); 8.10 (m, 3H); 8.03 (s, 1H); 7.96 (s, 1 H); 7.79 (d, 1H); 7.59 (d, 1H); 7.43 (br s, 2H); 6.61 (s, 2H); 4.59 (d, 1H); 4.51 (d, 1H); 3.26 (s, 3H); |
| 2-23 | N-[3-(7-Amino-1-methyl-2-oxo-1,4-dihydro-2H-pyrimido[4,5-d]pyrimidin-3-yl)-4-chloro-phenyl]-4-pyridin-4-yl-benzamide | (400 MHz, [D₆]-DMSO): δ = 10.58(s, 1H); 8.69 (br d, 2H); 8.11 (d, 2H); 8.05-7.90 (m, 4H); 7.79 (m, 3H); 7.58 (d, 1H); 6.59 (s, 2H); 4.60 (d, 1H); 4.49 (d, 1H); 3.26 (s, 3 H); |
| 2-24 | N-[3-(7-Amino-1-methyl-2-oxo-1,4-dihydro-2H-pyrimido[4,5-d]pyrimidin-3-yl)-4-chloro-phenyl]-4-(1H-pyrrol-2-yl)-benzamide | (400 MHz, CD₃OD): δ = 8.68 (s, 1H); 7.82 (m, 4H); 7.63 (dd, 1H); 7.59 (d, 1H); 7.42 (d, 1H); 6.78 (br s, 1H); 6.54 (br s, 1H); 6.10 (br s, 1H); 4.53 (dd, 2H); 3.28 (s, 3H); |
| 2-25 | 4'-Morpholin-4-ylmethyl-biphenyl-4-carboxylic acid [3-(7-amino-1-methyl-2-oxo-1,4-dihydro-2H-pyrimido[4,5-d]pyrimidin-3-yl)-4-chloro-phenyl]-amide | (400 MHz, CDCl₃): δ = 8.77 (s, 1H); 7.93 (d, 2H); 7.84 (d, 2H); 7.62 (d, 2H); 7.53 (d, 2H); 7.38 (m, 3H); 7.27 (d, 1H); 4.96 (s, 2H); 4.58 (d, 1H); 4.47 (d, 1H); 3.69 (t, 4H); 3.51 (s, 2H); 3.38 (s, 3H); 2.44 (t, 4H); |
| 2-26 | 3'-(4-Methyl-piperazin-1-ylmethyl)-biphenyl-4-carboxylic acid [3-(7-amino-1-methyl-2-oxo-1,4-dihydro-2H-pyrimido[4,5-d]pyrimidin-3-yl)-4-chloro-phenyl]-amide | (400 MHz, CDCl₃): δ = 8.60 (s, 1H); 7.81 (d, 2H); 7.77 (s, 1H); 7.71 (s, 1H); 7.51 (d, 2H); 7.41 (s, 1H); 7.35 (d, 1H); 7.21-7.10 (m, 4H); 4.87 (s, 2H); 4.46 (d, 1H); 4.35 (d, 1H); 3.46 (s, 2H); 3.27 (s, 3H); 2.48 (br s, 8H); 2.25 (s, 3H); |
| 2-27 | 3'-(4-Acetyl-piperazin-1-ylmethyl)-biphenyl-4-carboxylic acid [3-(7-amino-1-methyl-2-oxo-1,4-dihydro-2H-pyrimido[4,5-d]pyrimidin-3-yl)-4-chloro-phenyl]-amide | (400 MHz, [D₆]-DMSO): δ = 10.41 (s, 1H); 7.97 (d, 2H); 7.90 (s, 1H); 7.84 (s, 1H); 7.76 (d, 2H); 7.67 (d, 1H); 7.54-7.42 (m, 5H); 4.47 (d, 1H); 4.36 (d, 1H); 3.60 (s, 2H); 3.43 (m, 4H); 3.39 (s, 3H); 2.42 (m, 2H); 2.34 (m, 2H); 1.93 (s, 3 H); |
| 2-28 | 3'-Morpholin-4-ylmethyl-biphenyl-4-carboxylic acid [3-(7-amino-1-methyl-2-oxo-1,4- | (400 MHz, CDCl₃): δ = 8.98 (s, 1H); 7.98 (d, 2H); 7.95 (s, 1H); 7.88 (s, 1H); 7.71-7.67 (m, 3H); 7.55 (d, |

| Example-No. | Compound name | $^1$H-NMR |
|---|---|---|
| | dihydro-2H-pyrimido[4,5-d]pyrimidin-3-yl)-4-chloro-phenyl]-amide | 1H); 7.46-7.38 (m, 3H); 7.32 (d, 1H); 5.05 (s, 2H); 4.64 (d, 1H); 4.53 (d, 1H); 3.81 (t, 4H); 3.69 (s, 2H); 3.45 (s, 3H); 2.61 (br s, 4H); |
| 2-29 | 3'-(1-Carbamoyl-ethylsulfanyl)-biphenyl-4-carboxylic acid [3-(7-amino-1-methyl-2-oxo-1,4-dihydro-2H-pyrimido[4,5-d]pyrimidin-3-yl)-4-chloro-phenyl]-amide | (400 MHz, [D$_6$]-DMSO): δ = 10.55 (s, 1H); 8.07-8.01 (m, 3H); 7.97 (s, 1H); 7.86 (d, 1H); 7.80 (d, 2H); 7.73 (m, 1H); 7.70-7.50 (m, 3H); 7.49-40 (m, 2H); 7.12 (br s, 2H); 6.75 (br s; 1H); 4.62 (d, 1H); 4.50 (d, 1H); 3.98 (q, 1H); 3.27 (s, 3 H); 1.39 (d, 3H); |
| 2-30 | 3'-(2-Dimethylamino-ethoxy)-biphenyl-4-carboxylic acid [3-(7-amino-1-methyl-2-oxo-1,4-dihydro-2H-pyrimido[4,5-d]pyrimidin-3-yl)-4-chloro-phenyl]-amide; compound with acetic acid | (400 MHz, [D$_6$]-DMSO): δ = 10.58 (s, 1H); 9.93 (br s, 1H); 8.31 (s, 1H); 8.09 (m, 2H); 8.01 (s, 1H); 7.87 (d, 2 H); 7.80 (dd, 1H); 7.59 (d, 1H); 7.46 (t, 1H); 7.34 (m, 2H); 7.28 (br s; 2H); 7.07 (d, 1H); 4.64 (d, 1H); 4.53 (d, 1H); 4.45 (t, 2 H); 3.55 (t, 2H); 3.29 (s, 3H); 2.89 (s, 6H); 2.32 (s, 3 H); |

LIST OF REFERENCES

Bastin, R. J., et al., Organic Proc. Res. Dev. 4 (2000) 427-435
Biscardi, J. S., et al., Adv. Cancer Res. 76 (2000) 61-119
Merrifield, Fed. Proc. Fed. Amer. Soc. Exp. Biol. 21 (1962) 412
Stahl, P. H., and Wermuth, G., (editors), Handbook of Pharmaceutical Salts, Verlag Helvetica Chimica Acta (VHCA), Zürich (2002)
Susva, M., et al., Trends Pharmacol. Sci. 21 (2000) 489-495
WO 00/24744
WO 01/29041
WO 01/29042
WO 04/11465
WO 04/18472
WO 04/41821
WO 04/41822
WO 04/41823
WO 99/61444

The invention claimed is:

1. A compound according to formula I,

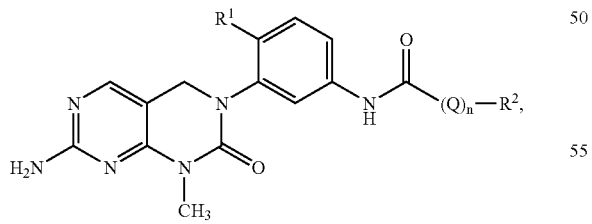

formula I wherein:
R$^1$ is chlorine;
Q is alkylene or alkenylene;
n is 0 or 1; and
R$^2$ is selected from the group consisting of:
(a) cycloalkyl;
(b) aryl, which is optionally substituted one or two times by phenyl, pyridyl, pyrrolyl, or indolyl; wherein said aryl, including said optional aromatic substituents, may be further optionally substituted one to three times by a substituent selected from the group consisting of:
(1) —CN;
(2) —CHO;
(3) —OH;
(4) —O-alkyl;
(5) —NH$_2$;
(6) —NH-alkyl;
(7) -alkyl-NH$_2$;
(8) alkyl;
(9) halogen;
(10) piperidinyl;
(11) piperazinyl;
(12) N-methyl-piperazinyl;
(13) morpholinyl;
(14) 2-dimethylamino-ethoxy;
(15) 1-carbamoyl-ethylsulfanyl;
(16) N-methyl-piperazinylmethyl;
(17) N-acetyl-piperazinylmethyl; and
(18) morpholinylmethyl; and
(c) heteroaryl, which is optionally substituted one or two times by phenyl, pyridyl, pyrrolyl, or indolyl; wherein said heteroaryl, including said optional aromatic substituents, may be further optionally substituted one to three times by a substituent selected from the group consisting of:
(1) —CN;
(2) —CHO;
(3) —OH;
(4) —O-alkyl;
(5) —NH$_2$;
(6) —NH-alkyl;
(7) -alkyl-NH$_2$;
(8) alkyl;
(9) halogen;
(10) piperidinyl;
(11) piperazinyl;
(12) N-methyl-piperazinyl;
(13) morpholinyl;
(14) 2-dimethylamino-ethoxy;

(15) 1-carbamoyl-ethylsulfanyl;
(16) N-methyl-piperazinylmethyl;
(17) N-acetyl-piperazinylmethyl; and
(18) morpholinylmethyl;
or a pharmaceutically-acceptable salt thereof.

2. A compound according to claim 1, wherein n is 0.

3. A compound according to claim 1, wherein n is 1.

4. A compound according to claim 1, wherein $R^2$ is selected from the group consisting of:
(a) cycloalkyl;
(b) aryl, which is optionally substituted one or two times by phenyl, pyridyl, pyrrolyl, or indolyl; wherein said aryl, including said optional aromatic substituents, may be further optionally substituted one to three times by a substituent selected from the group consisting of:
   (1) —CN;
   (2) —CHO;
   (3) —OH;
   (4) —O-alkyl;
   (5) —$NH_2$;
   (6) —NH-alkyl;
   (7) -alkyl-$NH_2$;
   (8) alkyl;
   (9) halogen;
   (10) piperidinyl;
   (11) piperazinyl;
   (12) N-methyl-piperazinyl; and
   (13) morpholinyl.
(c) heteroaryl, which is optionally substituted one or two times by phenyl, pyridyl, pyrrolyl, or indolyl; wherein said heteroaryl, including said optional aromatic substituents, being further optionally substituted one to three times by a substituent selected from the group consisting of:
   (1) —CN;
   (2) —CHO;
   (3) —OH;
   (4) —O-alkyl;
   (5) —$NH_2$;
   (6) —NH-alkyl;
   (7) -alkyl-$NH_2$;
   (8) alkyl;
   (9) halogen;
   (10) piperidinyl;
   (11) piperazinyl;
   (12) N-methyl-piperazinyl; and
   (13) morpholinyl.

5. A compound according to claim 1 selected from the group consisting of:
Cyclohexanecarboxylic acid (4-chloro-3-{7-amino-1-methyl-2-oxo-1,4-dihydro-2H-pyrimido[4,5-d]pyrimidin-3-yl}-phenyl)-amide; with acetic acid;
Cycloheptanecarboxylic acid(4-chloro-3-{7-amino-1-methyl-2-oxo-1,4-dihydro-2H-pyrimido[4,5-d]pyrimidin-3-yl}-phenyl)-amide; with acetic acid;
Biphenyl-4-carboxylic acid(4-chloro-3-{7-amino-1-methyl-2-oxo-1,4-dihydro-2H-pyrimido[4,5-d]pyrimidin-3-yl}-phenyl)-amide; and
Biphenyl-2-carboxylic acid(4-chloro-3-{7-amino-1-methyl-2-oxo-1,4-dihydro-2H-pyrimido[4,5-d]pyrimidin-3-yl}-phenyl)-amide; with acetic acid.

6. A compound according to claim 1 selected from the group consisting of:
Biphenyl-3-carboxylic acid(4-chloro-3-{7-amino-1-methyl-2-oxo-1,4-dihydro-2H-pyrimido[4,5-d]pyrimidin-3-yl}-phenyl)-amide; with acetic acid;
4'-Cyano-biphenyl-3-carboxylic acid(4-chloro-3-{7-amino-1-methyl-2-oxo-1,4-dihydro-2H-pyrimido[4,5-d]pyrimidin-3-yl}-phenyl)-amide;
N-[3-(7-Amino-1-methyl-2-oxo-1,4-dihydro-2H-pyrimido[4,5-d]pyrimidin-3-yl)-4-chloro-phenyl]-4-(4-methyl-piperazin-1-yl)-benzamide; and
N-[3-(7-Amino-1-methyl-2-oxo-1,4-dihydro-2H-pyrimido[4,5-d]pyrimidin-3-yl)-4-chloro-phenyl]-4-morpholin-4-yl-benzamide.

7. A compound according to claim 1 selected from the group consisting of:
N-[3-(7-Amino-1-methyl-2-oxo-1,4-dihydro-2H-pyrimido[4,5-d]pyrimidin-3-yl)-4-chloro-phenyl]-4-cyano-benzamide;
N-[3-(7-Amino-1-methyl-2-oxo-1,4-dihydro-2H-pyrimido[4,5-d]pyrimidin-3-yl)-4-chloro-phenyl]-4-phenyl-butyramide;
N-[3-(7-Amino-1-methyl-2-oxo-1,4-dihydro-2H-pyrimido[4,5-d]pyrimidin-3-yl)-4-chloro-phenyl]-3-phenyl-propionamide; and
N-[3-(7-Amino-1-methyl-2-oxo-1,4-dihydro-2H-pyrimido[4,5-d]pyrimidin-3-yl)-4-chloro-phenyl]-3-(2-hydroxy-phenyl)-propionamide.

8. A compound according to claim 1 selected from the group consisting of:
N-[3-(7-Amino-1-methyl-2-oxo-1,4-dihydro-2H-pyrimido[4,5-d]pyrimidin-3-yl)-4-chloro-phenyl]-3-(3-amino-phenyl)-propionamide;
N-[3-(7-Amino-1-methyl-2-oxo-1,4-dihydro-2H-pyrimido[4,5-d]pyrimidin-3-yl)-4-chloro-phenyl]-3-(4-amino-phenyl)-propionamide;
N-[3-(7-Amino-1-methyl-2-oxo-1,4-dihydro-2H-pyrimido[4,5-d]pyrimidin-3-yl)-4-chloro-phenyl]-3-phenyl-acrylamide; and
Naphthalene-1-carboxylic acid[3-(7-amino-1-methyl-2-oxo-1,4-dihydro-2H-pyrimido[4,5-d]pyrimidin-3-yl)-4-chloro-phenyl]-amide.

9. A compound according to claim 1 selected from the group consisting of:
1H-Indole-2-carboxylic acid[3-(7-amino-1-methyl-2-oxo-1,4-dihydro-2H-pyrimido [4,5-d]pyrimidin-3-yl)-4-chloro-phenyl]-amide;
N-[3-(7-Amino-1-methyl-2-oxo-1,4-dihydro-2H-pyrimido[4,5-d]pyrimidin-3-yl)-4-chloro-phenyl]-2-pyridin-3-yl-acetamide;
N-[3-(7-Amino-1-methyl-2-oxo-1,4-dihydro-2H-pyrimido[4,5-d]pyrimidin-3-yl)-4-chloro-phenyl]-2-pyridin-2-yl-acetamide; and
N-[3-(7-Amino-1-methyl-2-oxo-1,4-dihydro-2H-pyrimido[4,5-d]pyrimidin-3-yl)-4-chloro-phenyl]-3-pyridin-3-yl-propionamide.

10. A compound according to claim 1 selected from the group consisting of:
N-[3-(7-Amino-1-methyl-2-oxo-1,4-dihydro-2H-pyrimido[4,5-d]pyrimidin-3-yl)-4-chloro-phenyl]-3-pyridin-2-yl-acrylamide;
Benzo[b]thiophene-2-carboxylic acid(4-chloro-3-{7-amino-1-methyl-2-oxo-1,4-dihydro-2H-pyrimido[4,5-d]pyrimidin-3-yl}-phenyl)-amide;
N-[3-(7-Amino-1-methyl-2-oxo-1,4-dihydro-2H-pyrimido[4,5-d]pyrimidin-3-yl)-4-chloro-phenyl]-4-pyridin-2-yl-benzamide;
N-[3-(7-Amino-1-methyl-2-oxo-1,4-dihydro-2H-pyrimido[4,5-d]pyrimidin-3-yl)-4-chloro-phenyl]-4-pyridin-4-yl-benzamide; and N-[3-(7-Amino-1-methyl-2-oxo-1,4-dihydro-2H-pyrimido[4,5-d]pyrimidin-3-yl)-4-chloro-phenyl]-4-(1H-pyrrol-2-yl)-benzamide.

11. A compound according to claim 1, wherein n is 0 and $R^2$ is phenyl which is optionally substituted one time by phenyl, wherein said phenyl groups may be optionally substituted one time by a substituent selected from the group consisting of:
(a) 2-dimethylamino-ethoxy;
(b) 1-carbamoyl-ethylsulfanyl;
(c) N-methyl-piperazinylmethyl;
(d) N-acetyl-piperazinylmethyl; and
(e) morpholinylmethyl.

12. A compound according to claim 1 selected from the group consisting of:
4'-Morpholin-4-ylmethyl-biphenyl-4-carboxylic acid[3-(7-amino-1-methyl-2-oxo-1,4-dihydro-2H-pyrimido[4,5-d]pyrimidin-3-yl)-4-chloro-phenyl]-amide;
3'-(4-Methyl-piperazin-1-ylmethyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide; and
3'-(4-Acetyl-piperazin-1-ylmethyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide.

13. A compound according to claim 1 selected from the group consisting of:
3'-Morpholin-4-ylmethyl-biphenyl-4-carboxylic acid[3-(7-amino-1-methyl-2-oxo-1,4-dihydro-2H-pyrimido[4,5-d]pyrimidin-3-yl)-4-chloro-phenyl]-amide;
3'-(1-Carbamoyl-ethylsulfanyl)-biphenyl-4-carboxylic acid[3-(7-amino-1-methyl-2-oxo-1,4-dihydro-2H-pyrimido[4,5-d]pyrimidin-3-yl)-4-chloro-phenyl]-amide; and
3'-(2-Dimethylamino-ethoxy)-biphenyl-4-carboxylic acid [3-(7-amino-1-methyl-2-oxo-1,4-dihydro-2H-pyrimido[4,5-d]pyrimidin-3-yl)-4-chloro-phenyl]-amide; with acetic acid.

14. A pharmaceutical composition comprising a therapeutically effective amount of a compound of claim 1 and a pharmaceutically acceptable carrier.

15. A process for the manufacture of a compound according to claim 1 comprising:

(a) reacting the amino group of a compound according to formula II:

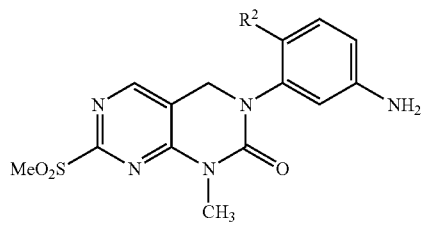

wherein $R^2$ is defined as in claim 1, with a carboxylic acid of the general formula III:

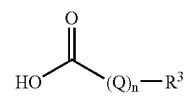

wherein $R^3$ is defined as in claim 1, to obtain the amide derivative of formula IV:

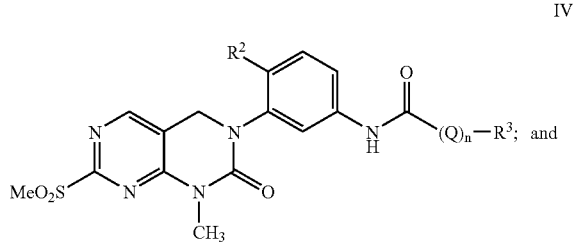

(b) converting the methylsulfonyl group of the amide derivative of formula IV to $NH_2$.

* * * * *